United States Patent [19]

Hata et al.

[11] Patent Number: 5,215,630
[45] Date of Patent: Jun. 1, 1993

[54] METHOD OF PURIFYING EICOSAPENTAENOIC ACID OR THE ESTER DERIVATIVE THEREOF BY FRACTIONAL DISTILLATION

[75] Inventors: Kazuhiko Hata, Kanagawa; Hideo Noda, Hyogo; Masahiro Makuta, Tokyo, all of Japan

[73] Assignees: Nippon Suisan Kaisha, Ltd., Tokyo; Kansai Chemical Engineering Co., Ltd., Hyogo, both of Japan

[21] Appl. No.: 709,991

[22] Filed: Jun. 4, 1991

[51] Int. Cl.$^5$ .......................... B01D 3/10; B01D 3/34
[52] U.S. Cl. ........................................ 203/38; 203/46; 203/73; 203/74; 203/75; 203/77; 554/175; 554/186
[58] Field of Search ........................ 203/75, 77, 73, 74, 203/43, 44, 38, 91, 45, 46; 260/419, 420, 428, 428.5; 554/185, 186, 175

[56] References Cited

U.S. PATENT DOCUMENTS

| | | | |
|---|---|---|---|
| 4,377,526 | 3/1983 | Fujita et al. | 260/419 |
| 4,675,132 | 6/1987 | Stout et al. | 260/428.5 |
| 4,804,555 | 2/1989 | Marschner et al. | 260/428 |
| 4,971,660 | 11/1990 | Rivers | 260/428 |
| 5,023,100 | 6/1991 | Chang et al. | 260/428 |
| 5,077,202 | 12/1991 | Seto et al. | 260/420 |

Primary Examiner—Wilbur Bascomb, Jr.
Attorney, Agent, or Firm—Wenderoth, Lind & Ponack

[57] ABSTRACT

The present invention provides a continuous method of purifying eicosapentaenoic acid and esters of eicosapentanoic acid, comprising (a) fractionally distilling a starting mixture containing eicosapentaenoic acid or esters of eicosapentaenoic acid using a system of at least three distillation columns connected in flow arrangement to separate a fraction containing eicosapentaenoic acid or esters of eicosapentaenoic acid and other $C_{20}$ fatty acids from a fraction containing lower-number carbon fatty acids and from a fraction containing higher-number carbon fatty acids, and (b) continuously collecting the fraction containing eicosapentaenoic acid or esters of eicosapentaenoic acid, wherein the pressure in the distillation columns is maintained at 10 Torr or below and wherein the bottom temperature of the distillation columns is maintained at 210° C. or below.

The present invention also provides a method of producing said products; using a continuous distillation process and urea adduct process by a specific apparatus construction.

15 Claims, 4 Drawing Sheets

METHOD OF PURIFYING EICOSAPENTAENOIC ACID OR THE ESTER DERIVATIVE THEREOF BY FRACTIONAL DISTILLATION

BACKGROUND OF THE INVENTION

1. Field of the Invention

The present invention relates to a method for producing a high-concentration eicosapentaenoic acid or the ester derivative thereof, more specifically to a new method of producing, at high efficiency, a high-concentration form of eicosapentaenoic acid (EPA) or the ester derivative thereof which is effective as a prescription medicine for the prevention of thrombosis and for the medical treatment and prevention of thrombus-induced diseases.

2. Description of Related Art

Eicosapentaenoic acid (EPA), and the ester, amide or other derivatives thereof, have been conventionally known as being effective as a prescription medicine for the prevention of thrombosis and for the medical treatment of thrombus-induced diseases.

It is known that eicosapentaenoic acid (EPA) and the derivatives thereof are contained per se, or in the form of a glyceride and other derivatives thereof, in natural fats and oils, particularly in fats and oils of mackerel, sardine, cod and other marine products. Studies have been made concerning the methods for taking out eicosapentaenoic acid from these fish oils.

However, these oils contain an overwhelming quantity of fatty acids with a carbon number of less than 19 and more than 21, i.e. other than eicosapentaenoic acid, which is an unsaturated fatty acid with a carbon number of 20. This makes it exceedingly difficult to efficiently and selectively purify eicosapentaenoic acid alone as a high-concentration (high purity) product.

For example, a method has been proposed in which fatty acid mixtures from natural fats and oils are esterified, and subjected to precision fraction under reduced pressures and the resultant fraction is purified with a urea addition method to provide eicosapentaenoic acid from the natural fats and oils (Japanese Patent Provisional Publication No. 149400/82).

By this method, in which fatty acid mixtures from natural fats and oils are subjected to precision fraction under a reduced pressures of 10 mmHg, preferably of 0.1 to 0.01 mmHg at a single rectifying column filled with rings and the resulting products are rectified by the urea addition method, eicosapentaenoic acid in a concentration of some 80% can be obtained. By this method, however, a mere 30% of eicosapentaenoic acid ester exists in the $C_{20}$ fraction are obtained by the rectification. Such methods also requires complicated troublesome treatment processes, such as a treatment of the urea adduct and the subsequent distillation under reduced pressures. Even with these processes, it is exceedingly difficult to improve the concentration of the eicosapentaenoic acid ester to 85% or higher. Thus, by the foregoing method large quantities of and urea, a multiplicity of treatments with urea, become practically required, placing great limitations on the reduction of manufacturing costs as well as the improvement of production efficiency. There has therefore been a serious limitation to putting this method into practical application.

Almost concurrently with the above method, a method was proposed by the applicant of the present invention wherein two distillation columns are employed to subject fatty acid mixtures obtained from natural fats and oils to continuous distillation to provide approximately 50% eicosapentaenoic acid as the $C_{20}$ fraction, then the product is subjected to urea addition treatment and purification through column chromatography (Japanese Patent Provisional Publication No. 8037/1983). This improved method has substantially enhanced the efficiency of purifying EPA by a distillation process, but eicosapentaenoic acid and the ester derivative thereof still cannot be obtained in concentration (or purity) as high as 80% or more without the subsequent urea addition treatments. Even with the urea addition process, the method still remains unsuccessful in producing eicosapentaenoic acid and the ester derivative thereof in a concentration as high as 85% or higher. For this reason, there has been need for improvements in the purification process of EPA and its ester derivatives.

In order to produce eicosapentaenoic acid and the ester derivative thereof, effective as a medical prescription medicine, or for clinical purposes it is strongly desired to purify it in a concentration of 80% or more, preferably 85% or more in large quantities and at high efficiency. Yet, under the aforestated circumstances and such methods object has been unfulfilled.

SUMMARY OF THE INVENTION

The present invention has been made considering the aforestated circumstances, and it is designed to provide a method which makes it possible to overcome the shortcomings of the conventional production and purification methods so as to provide eicosapentaenoic acid and the ester derivative thereof in a concentration higher than 85% in a convenient fashion, at high efficiency and low costs.

In order to overcome the foregoing problems, the present invention provides a method of producing eicosapentaenoic acid and the ester derivative thereof in a concentration as high as 80% or more, characterized by placing fatty acids or the ester mixtures thereof obtained from the natural fats and oils including eicosapentaenoic acid and the ester derivative thereof to continuous distillation under a reduced pressure of 10 Torr or below and a bottom temperature of 210° C. or less.

The method comprises fractionally distilling a starting mixture containing eicosapentaenoic acid or esters of eicosapentaenoic acid using a system of at least three distillation columns connected in flow arrangement to separate a fraction containing eicosapentaenoic acid or esters of eicosapentaenoic acid and other $C_{20}$ fatty acids from a fraction containing lower-number carbon fatty acids and from a fraction containing higher-number carbon fatty acids, and continuously collecting the fraction containing eicosapentaenoic acid or esters of eicosapentaenoic acid. refluxing, to a pre-stage distillation column, bottom liquid at a rectifying column in a distillation column system comprised of 3 or more distillation columns, with the rectifying column for the initial fraction of low-carbon number fatty acids separated.

In the method according to the present invention, it is preferred to send the condensate of the top fraction obtained from the pre-stage or first distillation column to the rectifying or second column for the collection of the initial fraction containing the lower-number carbon containing fatty acids and to establish a rectifying or third column for collecting the main fraction which contains eicosapentaenoic acid and the ester derivative thereof and for collecting the fraction containing higher-number carbon fatty acids independently for continuous distillation.

The present invention also provides a method of producing eicosapentaenoic acid and the ester derivative thereof by placing fatty acids or the ester mixtures thereof obtained from the natural fats and oils including eicosapentaenoic acid and the ester derivative thereof to continuous distillation under a reduced pressure of 10 Torr or below and a bottom temperature of 210° C. or less, by means of the foregoing method, further including steps of bringing the main fraction containing the resultant eicosapentaenoic acid and the ester derivative thereof into contact with a solution urea in methanol to give urea adduct, putting the same to a drainage treatment with non-polar solvent and removing the non-polar solvent to provide eicosapentaenoic acid and the ester derivative thereof in a concentration as high as 85% or more.

DETAILED DESCRIPTION OF THE INVENTION

Figure 1:
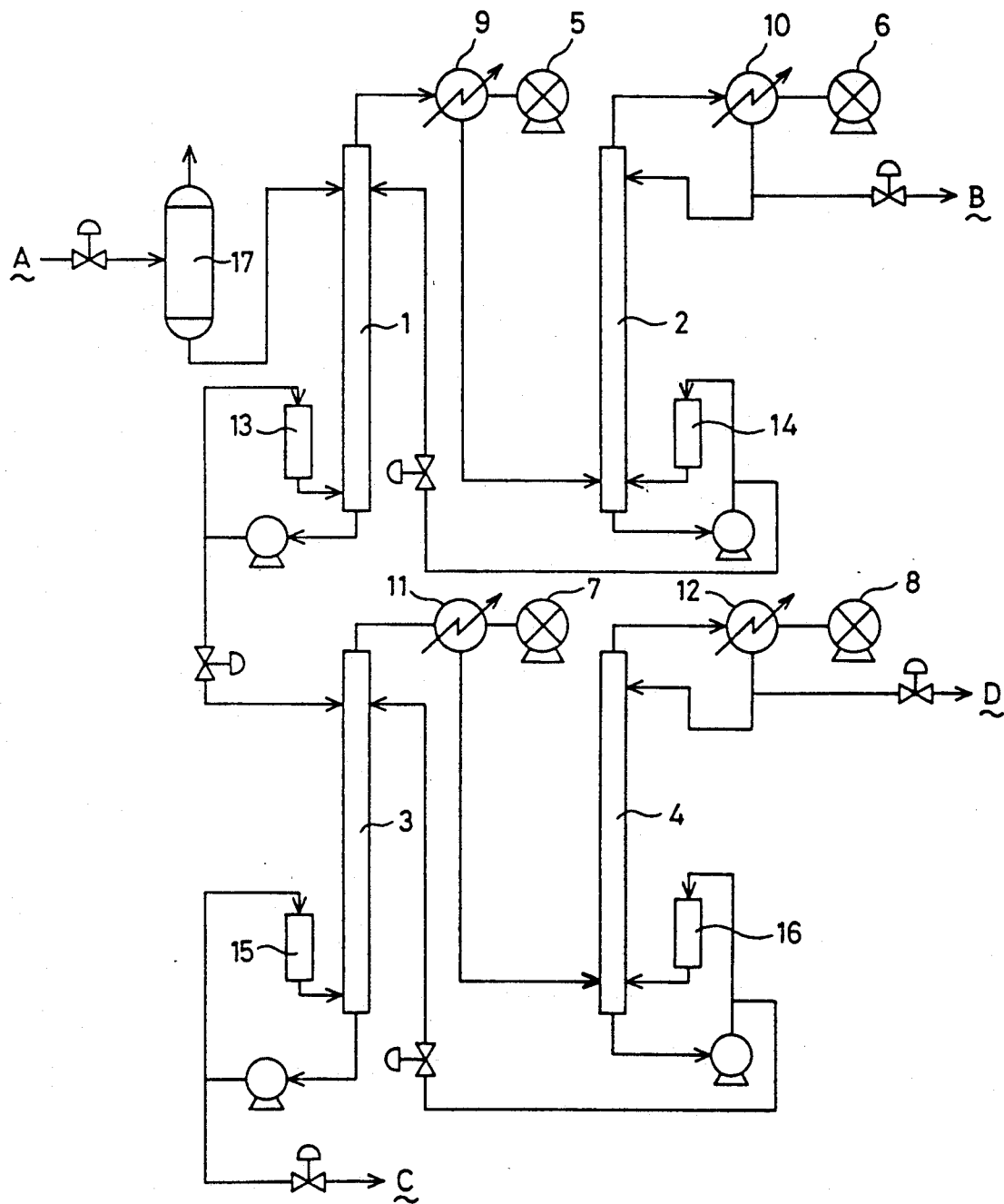
FIG. 1 is a drawing illustrating one embodiment of an apparatus for carrying out the present method of producing eicosapentaenoic acid and the ester derivative thereof through continuous distillation.

Eicosapentaenoic acids and other long-chain high-degree unsaturated fatty acids contain so many double bonds in the molecules thereof that they are apt to be subjected to degradation, polymerization and other thermal denaturation by the heat of a distillation process, rendering purfication of these fatty acids by a distillation process exceedingly difficult.

On the other hand, the natural fats and oils containing eicosapentaenoic acids also contain various kinds of fatty acids other than eicosapentaenoic acids, which have boiling points close to each other, and hence they cannot be separated unless a distillation column is used which is fairly high and the amount of reflux or recycling is increased. However, this causes thermal denaturation of the fatty acids due to rises in the bottom pressure of the column and the resultant temperature rise, making distillation purification of these acids even more difficult.

For these reasons, by the conventional methods, purification of EPA by a process distillation is controlled to a low level and those in the art are forced to purify the fatty acids to a high degree through urea addition and other processes at the subsequent stage. Inevitably, the load on the processes at the subsequent stages become larger.

The method according to the present invention provides eicosapentaenoic acid or the ester derivative thereof in a purity as high as 80% or 85% without the foregoing problems, in a simple operation requiring only distillation purification, and at high efficiency. It also becomes possible to purify the resultant eicosapentaenoic acid or the ester derivative thereof to a product in a concentration as high as 90% at extremely high efficiency by the subsequent urea addition processes.

As the fatty acid mixtures applicable to the method according to the present invention, any substances obtainable from natural fats and oils which contain quantities of eicosapentaenoic acid or the glyceride derivative thereof can be used. For instance, fatty acid mixtures from sardine, mackerel, herring, saury and other fish, Antarctic euphausian, and other animal marine plankton may be used.

These fatty acid mixtures are esterified for continuous distillation as desired.

As the continuous distillation method according to the present invention, filling spring type, column plate type and other various systems can be employed, and more preferably, a mesh plate can be used with a theoretical number of plates being more than 5.

Continuous distillation using 3 or more distillation columns according to the present invention is preferably accomplished under a reduced pressure of approximately 0.1 Torr and at 210° C. or below, or more preferably, at a bottom temperature of 195° C. or less.

The construction of this three-or-more column distillation apparatus is such that in any case, one column is made independent as a rectifying column for the collection of an initial containing the lower-carbon number fraction. For instance, in the case of a typical three-column construction, the columns are divided as follows:
(I) First distillation column;
(II) Second distillation column (rectifying column for the initial fraction);
(III) Third distillation column (rectifying column for the C20 main fraction and the residual fraction).

In the case of a four-column construction, the columns are divided as follows:
(I) First distillation column;
(II) Second distillation column (rectifying column for the initial fraction);
(III) Third distillation column (rectifying column for the residual fraction); and,
(IV) Fourth distillation column (rectifying column for the main fraction).

Furthermore, in the case of the three-column construction, the columns can be able divided as follows:
(I) First distillation column (rectifying column for the initial fraction);
(II) Second distillation column (rectifying column for the residual fraction); and,
(III) Third distillation column (rectifying column for the main fraction).

Needless to say, the construction of the rectifying columns can be further divided.

In any case in the method according to the present invention, it is essential that the bottom liquid of the rectifying column for the initial fraction be returned as reflux liquid to the first distillation column as in the above example. It is also preferably to condensate the top fraction of the first distillation column, then send it as condensate to the rectifying column for the initial fraction.

The main fraction of $C_{20}$ fatty acids obtainable through continuous distillation, i.e., the one containing eicosapentaenoic acid and the ester derivative is then subjected to urea treatment to provide a urea adduct. Then, the urea adduct is dissolved in methanol, ethanol and other highly soluble solvent to be used as urea adduct solution. Normally, the concentration of urea adduct is to be 5 to 20%.

Mixing the main $C_{20}$ fraction with this urea adduct solution is accomplished at a ratio of 0.5 to 10 parts relative to 1 part by weight of the main fraction. The mixture is subjected to forced cooling to room temperature or below, more preferably to 15° C. or less. Such treatment permits $C_{20}$ fatty acids having a lower degree of unsaturation, for example 1 to 4 unsaturated bonds to be separated as a compound material with urea.

Then, in the method according to the present invention, non-polar solvents, for instance, hexane and isooctane are added to a reaction mixture, the urea adduct and remaining urea are caused to shift to methanol layer, and the fatty acids to hexane layer for extraction and separation.

Then, in order to remove colored matter, oxides and other impurities as needed, the resulting substances are subjected to adsorption treatment via an adsorption column.

As the adsorption column, silica gel, activated clay, alumina and activated carbon can be used, but silica gel is the most preferred. Thereafter, the aforestated solvents are removed through distillation.

While referring to the drawings attached, a more detailed description will be given of the method according to the present invention.

Continuous distillation

FIG. 1 shows an example in which four distillation columns are used.

For instance, as indicated in this FIG. 1, the fatty acid mixture (A) is subjected to continuous distillation using four distillation columns (1), (2), (3) and (4).

At each of the distillation columns (1) (2) (3) and (4), vacuum systems (5) (6) (7) and (8), condenser systems (9) (10) (11) and (12) and reboilers (13) (14) (15) and (16) are also provided.

These distillation columns (1) (2) (3) and (4) are strictly controlled to have a reduced pressure of 10 Torr or below, and a bottom temperature of 210° C. or lower. The degree of vacuum is closely associated with temperature, and it is preferred but not essential that the vacuum systems (5) (6) (7) and (8) be made independent from one another. It is permissible to construct these vacuum systems arbitrarily in accordance with the capability and control systems of the vacuum pumps.

Under the aforestated construction, raw material (A) is introduced into the first distillation column (1), for instance in the vicinity of the top thereof, the top fraction is condensed by the condenser system (9) and is introduced in liquid form into a rectifying column as the second distillation column (2), for example at the bottom thereof. Such introduction of the top fraction in liquid form is one of the important factors in the method according to the present invention.

In the second distillation column (2), the initial fraction (B) consisting of fatty acids having a lower carbon number than desired (i.e. $<C_{19}$) is collected as the top fraction thereof. Some of the bottom liquid is refluxed to the vicinity of the top of the first distillation column (1). This is also a very important factor to the method of the present invention. The bottom condensate of the first distillation column (1) is heated with a reboiler (13) and returned to the bottom thereof, and at the same time, introduced in liquid form to the vicinity of the top of the third distillation column (3).

The top fraction of the third distillation column (3) is supplied to the bottom of the fourth distillation column (4) as condensate through a condenser system (11). The bottom distillate is heated with a reboiler (15) and returned to the bottom thereof, and concurrently the remaining fraction (C) consisting primarily of $C_{21}$ or greater fatty acids with longer chains than eicosapentaenoic acid or the ester derivative is collected.

At the fourth distillation column (4) into which condensate has been introduced from the top of the third distillation column (3), the fraction from the top is condensed by the condenser system (12), some of it being refluxed to the vicinity of the top while the main fraction (D) consisting primarily of eicosapentaenoic acid or the ester derivative is collected. On the other hand, the bottom condensate is heated with a reboiler (16) and returned to the bottom, and concurrently some of it is refluxed to the vicinity of the top of the third distillation column (3).

In addition, raw material (A) is treated at a flash tank (17) maintained at a reduced pressure prior to the introduction thereof into the first distillation column (1), removing air, water content and other impurities. It is advantageous to use a falling film evaporation type reboiler as the reboilers (13) (14) (15) and (16). This can effectively prevent thermal degradation of the fatty acids. (Continuous distillation and urea addition treatment)

Figure 2:
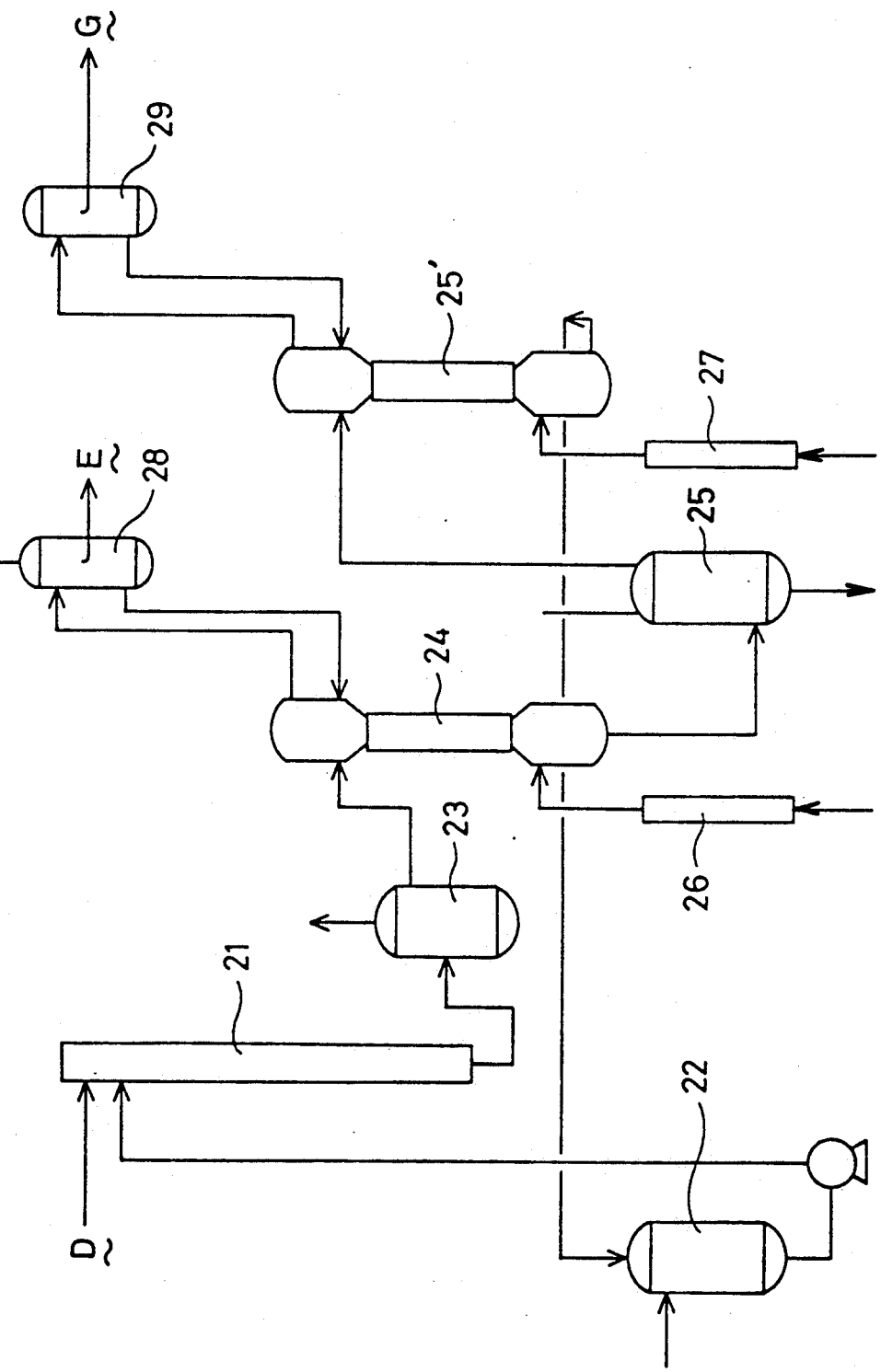
FIG. 2 is a drawing illustrating an apparatus for carrying out the urea-addition treatment processes following the continuous distillation.

FIG. 2 illustrates the process for formation of the urea adduct. The main fraction (D) containing eicosapentaenoic acid or the ester derivative in a concentration of 80% or higher is obtained by the foregoing continuous distillation.

As shown in FIG. 2, the main fraction (D) is sent to a column (21) in contact with a solution of urea, and, for instance, a solution of urea in methanol is guided from a tank (22) to be brought into contact with the column. At this time, the solution of urea in methanol is introduced at a temperature of 35° to 45° C., and is subjected to forced cooling at the column in contact therewith so that it is at or below room temperature.

Then, the treatment liquid is fed through a tank (23) to a product extraction column (24) using a non-polar solvent, e.g., n-hexane. The product solvent layer (E) which separates the solution of urea in methanol and the urea adduct is sent to the next process. The solution of urea in methanol and the urea adduct are fed to a tank (25), and after being subjected to thermal decomposition, they are subjected to another cycle of extraction treatment at a residue extracting column (25') to separate a residue solvent layer (G). The non-polar solvent is either cooled or heated at a cooling column (26) or a heating column (27) and fed to the extracting columns (24) (25'). The solvent layers (E) (G) are taken out of decanters (28) (29).

Figure 3:
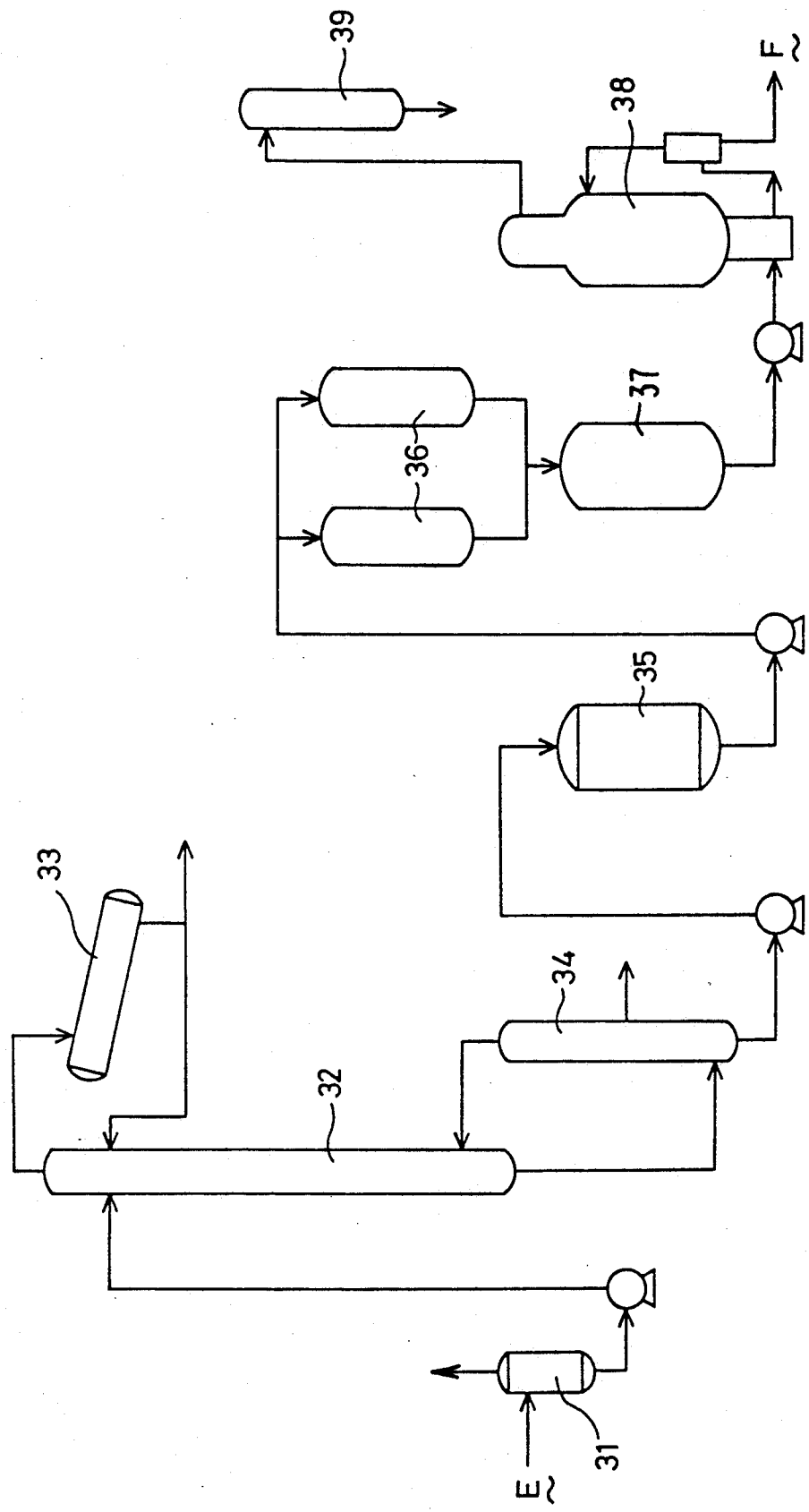
FIG. 3 is a drawing illustrating an apparatus for carrying out a purification process following the urea addition.

Then, the product solvent layer (E) is fed to a methanol rectifying column (32) through a tank (31) as indicated in FIG. 3. By the operation at the methanol rectifying column (32) in which a rectifying condenser (33) and a methanol evaporator (34) are provided, a product extracting solvent layer which is subjected to a treatment of removing methanol is obtained, and filtering the same removes the remaining urea.

Then, this substance is led to adsorption columns (36) and mixing bank (37) through a tank (35), removing colored matter, oxides and other impurities. Next, solvent, e.g., n-hexane, is removed using an evaporator (38).

An n-hexane condenser (39) is provided for this evaporator.

In this way, a product (F) can be obtained. The final concentration of the product (F) is increased to 85% or higher.

Specific examples of EPA production by the production method of the present invention will now be given using the systems shown in FIGS. 1 to 3.

PRODUCTION EXAMPLE 1

Using an apparatus as shown in FIG. 1, the ethylester in a fatty acid mixture (60% for $C_{19}$, 23% for $C_{20}$ and 17% for $C_{21}$) obtained from fish oil was treated at a flash tank (17) which is kept at a vacuum of 1 Torr, then supplied to the first distillation column (1) with a column diameter of 300 mm and a height of approx. 7 m and maintained at a vacuum of 0.1 Torr at a rate of 15 to 20 l/hr.

At this first distillation column (1), the bottom temperature was controlled at 194° to 195° C., and the top temperature at 124° to 125° C. Inside it, a 4 mm-mesh plate was provided, with the theoretical number of plates set at 4. Since fatty acid ester mixtures greater than $C_{20}$ are collected at the bottom of this first distillation column (1), it becomes difficult to control the degree of vacuum and temperature at the bottom thereof. Accordingly, the quantity of packing into the first distillation column was less than that in the second distillation column (2).

The top condensate of the first distillation column (1) was introduced into the bottom of the second distillation column (2). The bottom temperature of this second column was set at 184° to 185° C., while the top temperature was set at 100° to 111° C., with the column being operated under a reduced pressure of 0.1 Torr. The theoretical number of column plates was set at 6. The top fraction was refluxed at a reflux ratio of 1:2, some of it being collected as the initial fraction (B).

The composition of the initial fraction was, as indicated in Table 1, 99% for $C_{19}$ or lower fatty acids, 1% for $C_{20}$ eicosapentaenoic acid ester and others and 0% for $C_{21}$ or greater fatty acids.

The conditions of the second distillation column (2) were controlled so that the bottom condensate thereof was maintained and constant level, and said condensate was returned to the vicinity of the top of the first distillation column (1). In other words, the bottom condensate was returned as reflux liquid to the first distillation column (1).

The bottom liquid of the first distillation column (1) was fed to the vicinity of the top of the third distillation column (3). The pressure of the third distillation column (3) was a reduced pressure of 0.1 Torr, while the bottom temperature was 194° to 195° C. and the top temperature at 124° to 125° C. The theoretical number of column plates was 4.

As the bottom liquid of the third distillation column (3), the residual fraction (C) was collected. The residual fraction was, as indicated in Table 1, composed of 0.1% for $C_{18}$ or lower fatty acids, 20% for $C_{20}$ eicosapentaenoic acid ester and others and 79.9% for $C_{21}$ or greater fatty acids.

The top fraction of this third distillation column (3) was supplied to the fourth distillation column (4) as condensate. The fourth distillation column (4) with a theoretical number of column plates being 6 was operated under a reduced pressure of 0.1 Torr, at a bottom temperature of 194° to 195° C. and a top temperature of 110° to 111° C.

The bottom liquid was returned as reflux liquid to the top of the third distillation column (3). The level of the bottom liquid of the fourth distillation column was kept constant.

The top condensate was refluxed at a reflux ratio of 1 to 2, and at the same time, the main fraction (D) was collected.

The main fraction was, as indicated in Table 1, composed of 0.1% for $C_{19}$ or lower fatty acids, 0% for $C_{21}$ or greater fatty acids and 99.9% for $C_{20}$ eicosapentaenoic acid ester and others.

The concentration of eicosapentaenoic acid ethylester in the $C_{20}$ fraction was 88%.

COMPARATIVE EXAMPLE

Figure 4:
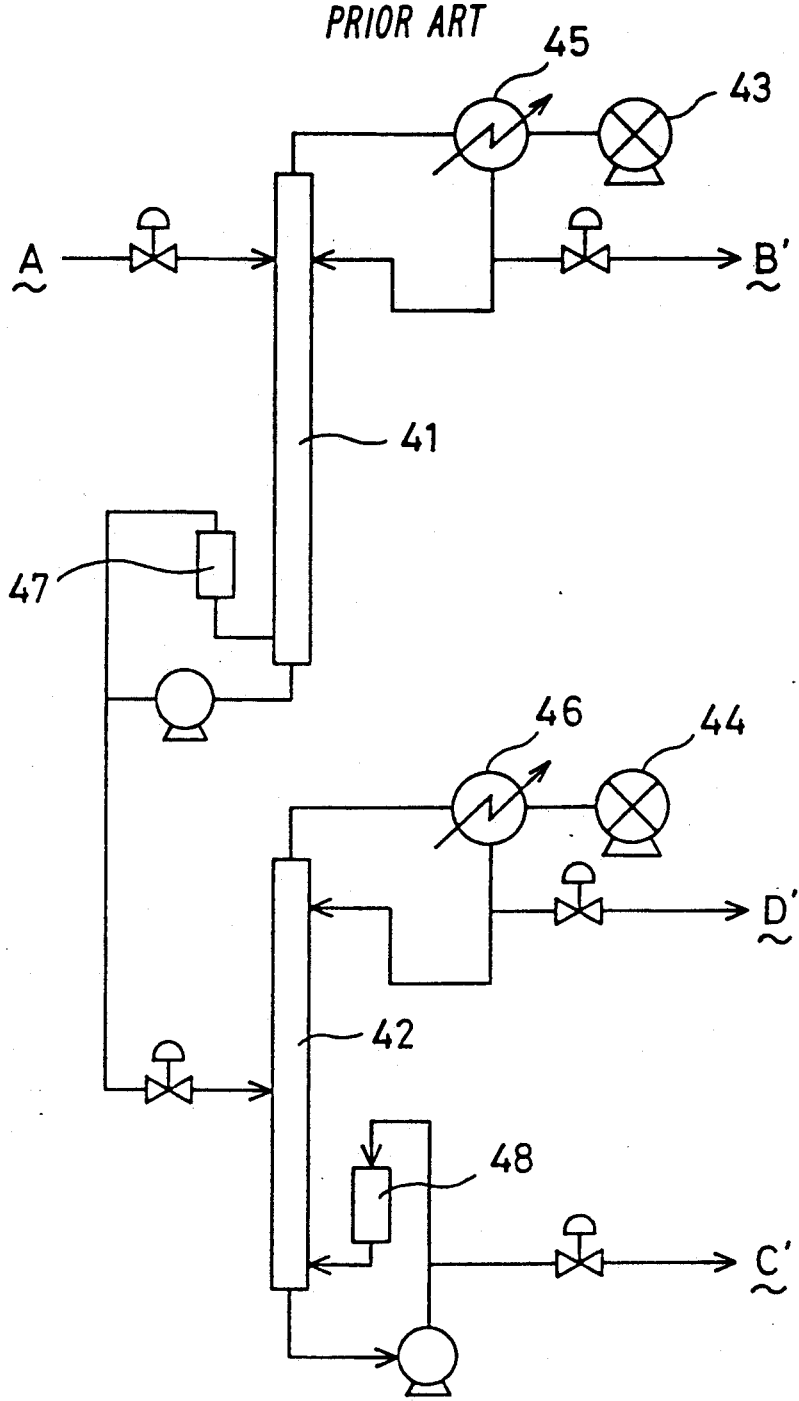
FIG. 4 is a drawing depicting an apparatus for carrying out the conventional two-column distillation method.

For comparison, continuous distillation was performed under reduced pressure using a two-column distillation column system (41) (42) (a theoretical number of column plates being 10) as shown in FIG. 4.

Again in this case, each of the distillation columns (41) (42) was provided with independent vacuum systems (43) (44) and condenser systems (45) (46), with a reboiler (47) (48).

The system was so designed that the initial fraction (B') was collected from the top of the first distillation column (41), the main fraction (D') was collected from the top of the second distillation column (42) and the residual fraction (C') was collected from the bottom thereof. Each of the distillation columns (41) (42) was under a reduced pressure of 0.1 Torr. In spite of the attempts to control the bottom temperature of the first distillation column (41) to 195° C. or lower, it was difficult to control the temperature; the bottom temperature would rise to 210° C. or higher.

The compositions of the initial fraction, main fraction and residual fraction were as indicated in Table 2. The efficiency of the separation/purification of $C_{20}$ fraction by this example proved to be far inferior to the method of the present invention, making it exceedingly difficult to control the distillation operation. Only 76% of the eicosapentaenoic acid ethylester of the main fraction which was collected as $C_{20}$ fraction was collected. Even though the bottom temperature of the first distillation column (41) was controlled to 195° C. or lower, as is evident from Table 2, fatty acids with lower carbon number, particularly $C_{18}$ fatty acids, were inevitably included, rendering the resultant product unsatisfactory.

TABLE 1

| Composition | Raw Material (A) | Initial Fraction (B) | Residual Fraction (C) | Main Fraction (product) (D) |
| --- | --- | --- | --- | --- |
| $<C_{19}$ | 60 | 99 | 0.1 | 0.1 |
| $C_{20}$ | 23 | 1 | 20 | 99.9 |
| $C_{21}<$ | 17 | 0 | 79.9 | 0 |

TABLE 2

| Composition | Raw Material (A) | Initial Fraction (B') | Residual Fraction (C') | Main Fraction (product) (D') |
| --- | --- | --- | --- | --- |
| $<C_{19}$ | 60 | 80 | 5.1 | 10.1 |
| $C_{20}$ | 23 | 20 | 20.0 | 89.9 |
| $C_{21}<$ | 17 | 0 | 74.9 | 0 |

PRODUCTION EXAMPLE 2

Using an apparatus as shown in FIG. 2, the main fraction (D) which contains 99.9% $C_{20}$ ethylester and 88% eicosapentaenoic acid ethylester, both obtained from Example 1, was brought into contact with a 15% solution of urea in methanol at a contact column (21). The temperature of this solution was 42° C., and it was subjected to forced cooling down to 10° C. in the contact column (21).

Using the n-hexane cooled to 10° C., the product was put to drainage treatment in an extraction column (24).

The product solvent layer (E) obtained was removed of methanol in a methanol-removing column (32), and further urea was filtered. The product solvent layer (E) contained the following components, but the methanol and urea were completely removed.

| | |
|---|---|
| Fatty acid ester | 12 to 13% |
| Methanol | 5% |
| Hexane | 82 to 83% |
| Trace amount of urea | |

The treatment liquid was then guided to silica gel adsorption columns (36) (37), colored matter, oxides and other impurities were removed, and hexane was removed in an evaporator (38), providing eicosapentaenoic acid ethylester product (F). The concentration thereof was 93%.

As has been described in detail, the method of the present invention can provide eicosapentaenoic acid and the ester derivative thereof having a concentration (purity) of 85% or higher, even 90% or higher. It can also produce the desired product at high efficiency.

What I claim:

1. A method for purifying eicosapentaenoic acid and esters of eicosapentaenoic acid, comprising:
   fractionally distilling a mixture containing eicosapentaenoic acid or esters of eicosapentaenoic acid using a system of at least three distillation columns connected in flow arrangement to separate a fraction containing eicosapentaenoic acid or esters of eicosapentaenoic acid and other $C_{20}$ fatty acids from a fraction containing lower-number carbon fatty acids and from a fraction containing higher-number carbon fatty acids,
   wherein the pressure in the distillation columns is maintained at 10 Torr or below and wherein the bottom temperature of the distillation columns is maintained at 210° C. or below, and
   collecting the fraction containing eicosapentaenoic acid or esters of eicosapentaenoic acid.

2. The method according to claim 1, wherein said fractional distillation step comprises feeding the mixture to a first distillation column, fractionally distilling the mixture to obtain a top fraction, condensing the top fraction, feeding the condensed top fraction to a second distillation column, fractionally distilling the condensed top fraction in the second column to obtain a top fraction, the top fraction in the second column being the fraction containing the lower-number carbon fatty acids, and removing the top fraction from the second column, thereby separating the fraction containing the lower-number carbon fatty acids from the fraction containing eicosapentaenoic acid or esters of eicosapentaenoic acid.

3. The method according to claim 1, wherein said fractional distillation step comprises feeding the mixture to a first distillation column, fractionally distilling the mixture to obtain a top fraction, condensing the top fraction, feeding the condensed top fraction to a second distillation column, fractionally distilling the condensed top fraction in the second column to obtain a bottom liquid fraction, and recycling the bottom liquid fraction in the second column to the top of the first distillation column.

4. The method according to claim 1, wherein said fractional distillation step comprises feeding the mixture to a first distillation column, fractionally distilling the mixture to obtain a bottom liquid fraction, feeding the bottom liquid fraction to a third column, and fractionally distilling the bottom liquid fraction in the third column to obtain a top fraction containing the eicosapentaenoic acid or esters of eicosapentaenoic acid and other $C_{20}$ fatty acids and a bottom liquid fraction containing the higher-number carbon fatty acids.

5. The method according to claim 4, wherein the top fraction containing the eicosapentaenoic acid or esters of eicosapentaenoic acid and other $C_{20}$ fatty acids obtained in the third column is fed to a fourth distillation column and further distilled to obtain a top fraction in the fourth column containing a more purified concentration of eicosapentaenoic acid or esters of eicosapentaenoic acid.

6. The method according to claim 1, wherein each of the distillation columns is equipped with an independent vacuum system and condenser system.

7. A continuous method for purifying eicosapentaenoic acid and esters of eicosapentaenoic acid, comprising:
   (a) feeding a starting mixture of eicosapentaenoic acid or esters of eicosapentaenoic acid to a first distillation column,
   (b) fractionally distilling the mixture using the first distillation column to obtain a bottom liquid fraction containing eicosapentaenoic acid or esters of eicosapentaenoic acid and higher-number carbon fatty acids and a top fraction containing lower-number carbon fatty acids,
   (c) condensing the top fraction and feeding it to a second distillation column, then fractionally distilling the condensed top fraction in the second column to obtain a top fraction containing the lower-number carbon fatty acids and a bottom liquid fraction, removing the top fraction from the second column to separate the fraction containing the lower-number carbon fatty acids from the system, and recycling the bottom liquid fraction in the second column to the first distillation column,
   while simultaneously feeding the bottom liquid fraction obtained in the first column to a third column, fractionally distilling the bottom liquid fraction in the third column to obtain a top fraction containing eicosapentaenoic acid or esters of eicosapentaenoic acid and a bottom liquid fraction containing the higher-number carbon fatty acids, removing the bottom liquid fraction from the third column to separate the fraction containing the higher-carbon number fatty acids from the system,
   (d) feeding the top fraction obtained in the third column to a fourth column, fractionally distilling the top fraction in the fourth column to obtain a top fraction containing purified eicosapentaenoic acid or esters of eicosapentaenoic acid, (e) collecting the top fraction containing purified eicosapentaenoic acid or esters of eicosapentaenoic acid, and (f) repeating steps (a) through (e), wherein the pressure in the distillation columns is maintained at 10 Torr or below and wherein the bottom temperature of the distillation columns is maintained at 210° C. or below.

8. A method for purifying eicosapentaenoic acid and esters of eicosapentaenoic acid, comprising:

fractionally distilling a mixture containing eicosapentaenoic acid or esters of eicosapentaenoic acid using a system of at least three distillation columns connected in flow arrangement to separate a fraction containing eicosapentaenoic acid or esters of eicosapentaenoic acid and other $C_{20}$ fatty acids from a fraction containing lower-number carbon fatty acids and from a fraction containing higher-number carbon fatty acids, wherein the pressure in the distillation columns is maintained at 10 Torr or below and wherein the bottom temperature of the distillation columns is maintained at 210° C. or below, collecting the fraction containing eicosapentaenoic acid or esters of eicosapentaenoic acid, treating the fraction containing eicosapentaenoic acid or esters of eicosapentaenoic acid with a solution of urea and a non-polar solvent to obtain a urea adduct, and removing the solvent by distillation to obtain a fraction containing concentrated eicosapentaenoic acid or esters of eicosapentaenoic acid.

9. The method according to claim 8, wherein said fractional distillation step comprises feeding the mixture to a first distillation column, fractionally distilling the mixture to obtain a top fraction, condensing the top fraction, feeding the condensed top fraction to a second distillation column, fractionally distilling the condensed top fraction in the second column to obtain a top fraction containing the lower-number carbon fatty acids, and removing the top fraction from the second column, thereby separating the fraction containing the lower-number carbon fatty acids from the fraction containing eicosapentaenoic acid or esters of eicosapentaenoic acid.

10. The method according to claim 8, wherein said fractional distillation step comprises feeding the mixture to a first distillation column, fractionally distilling the mixture to obtain a top fraction, condensing the top fraction, feeding the condensed top fraction to a second distillation column, fractionally distilling the condensed top fraction in the second column to obtain a bottom liquid fraction, and recycling the bottom liquid fraction in the second column to the first distillation column.

11. The method according to claim 8, wherein said fractional distillation step comprises feeding the mixture to a first distillation column, fractionally distilling the mixture to obtain a bottom liquid fraction, feeding the bottom liquid fraction to a third column, fractionally distilling the bottom liquid fraction in the third column to obtain a top fraction containing the eicosapentaenoic acid or esters of eicosapentaenoic acid and other $C_{20}$ fatty acids and a bottom liquid fraction containing the higher-number carbon fatty acids.

12. The method according to claim 11, wherein the top fraction containing the eicosapentaenoic acid or esters of eicosapentaenoic acid and other $C_{20}$ fatty acids obtained in the third column is fed to a fourth column and further distilled to obtain a top fraction containing a more purified concentration of eicosapentaenoic acid or esters of eicosapentaenoic acid.

13. The method according to claim 8, wherein each of the distillation columns is equipped with an independent vacuum system and condenser system.

14. The method according to claim 8, wherein the fraction containing eicosapentaenoic acid or esters of eicosapentaenoic acid is treated with a solution of urea in methanol at a temperature lower than room temperature.

15. The method according to claim 8, wherein the non-polar solvent is hexane.

* * * * *